US00PP36481P2

(12) United States Plant Patent
Grazzini

(10) Patent No.: US PP36,481 P2
(45) Date of Patent: Feb. 18, 2025

(54) ***COLEUS* PLANT NAMED 'G20057'**

(50) Latin Name: *Coleus scutellarioides*
Varietal Denomination: G20057

(71) Applicant: Richard A. Grazzini, Columbus, OH (US)

(72) Inventor: Richard A. Grazzini, Columbus, OH (US)

(73) Assignee: Garden Genetics llc, Columbus, OH (US)

( * ) Notice: Subject to any disclaimer, the term of this patent is extended or adjusted under 35 U.S.C. 154(b) by 0 days.

(21) Appl. No.: 18/816,414

(22) Filed: Aug. 27, 2024

(51) Int. Cl.
*A01H 5/12* (2018.01)
*A01H 6/50* (2018.01)

(52) U.S. Cl.
USPC ..... Plt./469
CPC ..... *A01H 6/50* (2018.05)

(58) Field of Classification Search
USPC ..... Plt./469
CPC ..... A01H 5/12
See application file for complete search history.

*Primary Examiner* — Kent L Bell
(74) *Attorney, Agent, or Firm* — Cassandra Bright

(57) ABSTRACT

A new and distinct cultivar of *Coleus* plant named 'G20057' is disclosed, characterized by a compact, densely branched habit. Leaves are highly dissected, with a fish skeleton-like appearance. Foliage has a dark red-purple central area, surrounded by a yellow-green picotee edge. Floral initiation begins in mid-August at 41N latitude, under natural day-length. The new cultivar is a *Coleus*, typically produced as an outdoor ornamental plant or for garden or container uses.

3 Drawing Sheets

Figure 1:
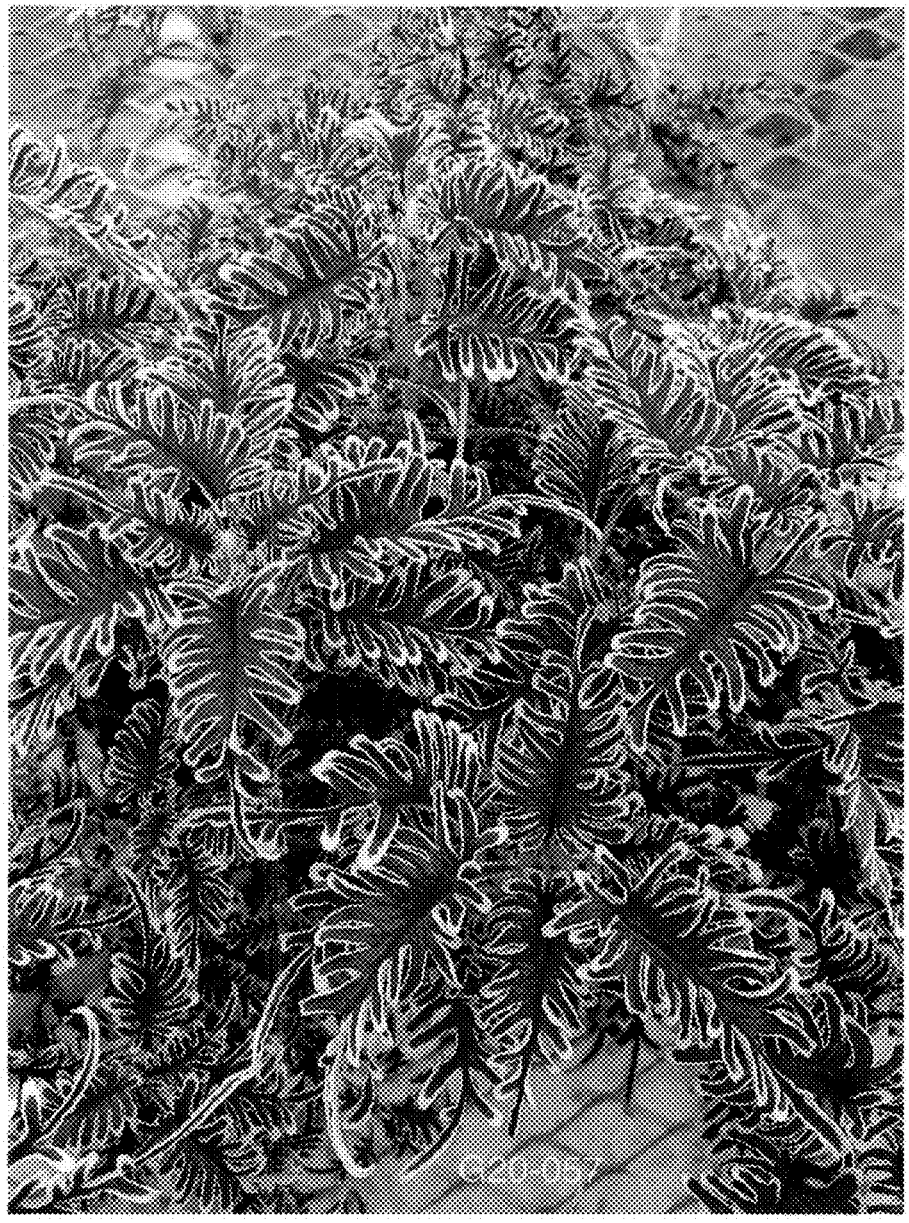

Latin name of the genus and species: *Coleus scutellarioides.*

Variety denomination: 'G20057'.

BACKGROUND OF THE INVENTION

The new cultivar is the product of a planned breeding program conducted by the inventor. The self-pollination resulting in the new variety was made in August of 2019 at a research greenhouse in Bellefonte, Pennsylvania. The parent variety is an undistributed, unpatented proprietary variety referred to internally as 'G18-082'. The new cultivar 'G20057' is a seedling derived from self-pollinating 'G18-082'. The parental variety 'G18-082' is an F1 hybrid selection between 2 unprotected proprietary breeding lines of the inventor. The new variety was found and selected by the inventor in March of 2020 at the same research greenhouse in Bellefonte, Pennsylvania.

Asexual reproduction of the new cultivar 'G20057' by terminal vegetative cuttings was performed at the same nursery in Bellefonte, Pennsylvania in March of 2020. Subsequent asexual reproduction has shown that the unique features of this cultivar are stable and reproduced true to type through successive generations.

SUMMARY OF THE INVENTION

The cultivar 'G20057' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G20057'. These characteristics in combination distinguish 'G20057' as a new and distinct *Coleus* cultivar:

1. Compact, densely branched habit.
2. Floral initiation begins in mid-August at 41N latitude, natural daylength.
3. Leaves are highly dissected, with a fish skeleton-like appearance.
4. Foliage has a dark red-purple central area, surrounded by a yellow-green picotee edge.
5. Mature plant is typically broader (40 cm) than tall (30 cm).

PARENT COMPARISON

Plants of the new cultivar 'G20057' are similar to plants of the parent variety, the unpatented *Coleus* 'G18-082', in most horticultural characteristics. However, plants of the new cultivar 'G20057' differ in the following ways:

1. 'G20057' is more compact and more densely branched than the parent 'G18-052'.
2. 'G20057' has more highly dissected leaves than 'G18-052'.
3. 'G20057' has a more narrow picotee edge to the leaf pattern than 'G18-052'.
4. 'G20057' has a longer, more narrow leaf than 'G18-052'.
5. Leaves of 'G20057' are more flat, and less ruffled than those of 'G18-052'.

COMMERCIAL COMPARISON

'G20057' can be compared to the commercially known variety *Coleus* 'ApBran', unpatented. These plants are similar in most horticultural characteristics. However, plants of the new cultivar 'G20057' differ in the following ways:

1. 'G20057' is more vigorous and less compact than 'ApBran'.

2. 'G20057' has more highly dissected foliage than 'ApBran'.
3. 'G20057' has more consistent marginal yellow-green picotee leaf edge than 'ApBran'.
4. 'G20057' blooms about 3 weeks earlier than 'ApBran' at 41N latitude, natural daylength
5. The central blotch on leaves of 'G20057' are lighter red-purple in color than that of 'ApBran'.

'G20057' can also be compared to the commercially known variety *Coleus* 'Balflamsira', U.S. Plant Pat. No. 32,342. These cultivars are similar in most horticultural characteristics. However, plants of the new cultivar 'G20057' differ in the following ways:

1. 'G20057' is more vigorous and less compact than 'Balflamsira'.
2. 'G20057' has more highly dissected foliage than 'Balflamsira'.
3. 'G20057' has a more sharply defined marginal yellow-green picotee leaf edge than 'Balflamsira'.
4. 'G20057' blooms about 2 weeks earlier than 'Balflamsira' at 41N latitude, natural daylength.
5. The central blotch of leaves of 'G20057' are lighter red-purple in color than that of 'Balflamsira'.

BRIEF DESCRIPTION OF THE PHOTOGRAPHS

The accompanying photograph in FIG. 1 illustrates a close-up view of the mature foliage on a plant of about 5 months old.

Figure 2:
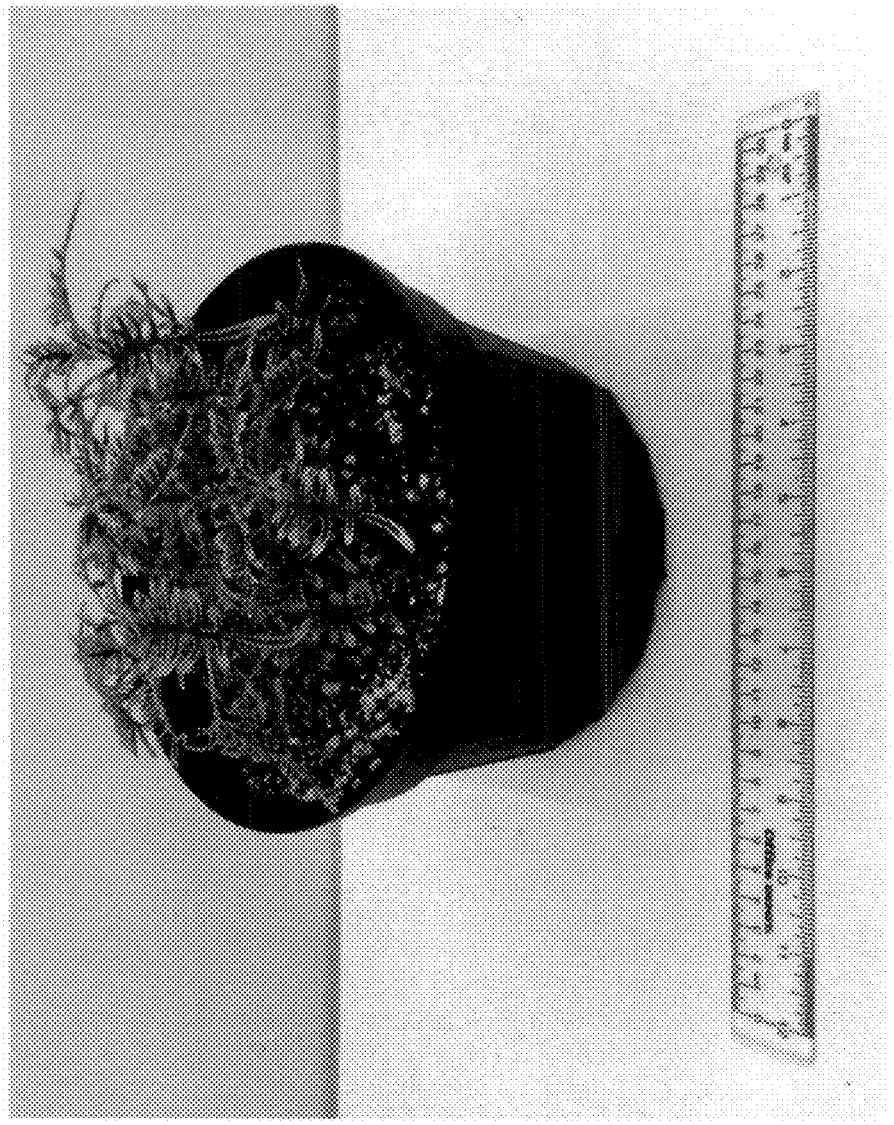

FIG. 2. illustrates a young plant of 'G20057' with immature foliage, grown in a greenhouse. The plant is approximately 2 months old in a 6-inch pot.

Figure 3:
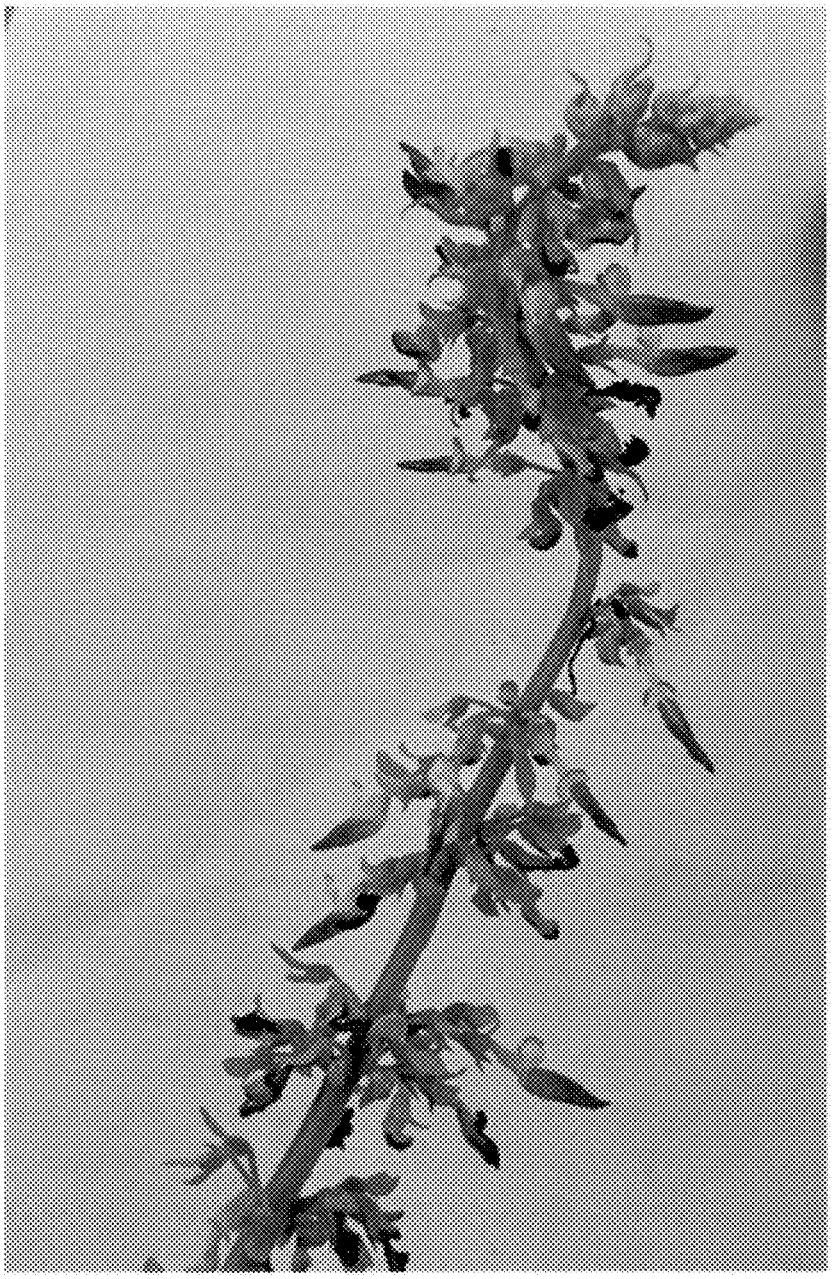

FIG. 3 is a photograph of a mature inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'G20057' plants grown outdoors from Spring to early Summer in Camarillo, California. The growing temperature ranged from about 7° C. to 30° C. during the day and from about 5° C. to 12° C. during the night. General light conditions are bright, normal sunlight. Measurements and numerical values represent averages of typical plant types. Plants are approximately 4 months old from a rooted cutting. No chemical or photoperiodic treatments were given.

Botanical classification: *Coleus scutellarioides* 'G20057'.

PROPAGATION

Root description: Fine, well-branched, fibrous, becoming slightly woody with age. Colored near Greyed-Yellow-161D and White 155A.

PLANT

Growth habit: Tender herbaceous perennial. Slightly flattened globular. Dense branching and foliage.

Height: Approximately 15 cm.

Plant spread: Approximately 18 cm.

Growth rate: Moderate.

Branching characteristics: Basal and lateral branching. Well branched both basally and laterally.

Length of branches: Approximately 9 to 15 cm.

Diameter branches: Approximately 5 to 6 mm.

Quantity of branches: Approximately 4 to 6 basal branches, each basal branch with 6 to 12 lateral branches.

Texture of lateral branches: Glabrous.

Color of lateral branches: Near RHS Yellow-Green 144C. Nodes heavily flushed Red-Purple 59C.

Aspect: Approximately 30° to 60° angle from center of plant.

Strength of lateral branches: Moderate.

Internode length: Average range 8 to 12 mm.

Age of plant described: Approximately 4 months old.

Foliage:

*Arrangement.*—Opposite.

*Average length.*—Average range 5.5 to 8 cm.

*Average width.*—Average range 2.3 to 3.7 cm.

*Shape of blade.*—Overall narrow ovate. Deeply and densely lobed. About 16 to 22 evenly spaced lobes per leaf. Uniformity of spacing creates a fish skeleton appearance. Lobe depth about 70% of overall leaf width.

*Apex.*—Rounded.

*Base.*—Cordate.

*Attachment.*—Petiolate.

*Margin.*—Entire along deep lobes.

*Texture of top surface.*—Sparsely pubescent.

*Texture of bottom surface.*—Sparsely pubescent with protruding veins.

*Foliage color.*—Young foliage upper side: Near RHS Greyed-Purple 183A, center vein 187A. Thick margin Yellow-Green N144B. Young foliage under side: Near RHS Greyed-Purple 183A, center vein 187B. Thick margin Yellow-Green N144B. Mature foliage upper side: Near RHS Red-Purple 58A, with some small blotches 58C center streak N186B. Thick margin Yellow-Green N144B. Mature foliage under side: Near RHS Greyed-Purple 185D, center streak 187D. Thick margin Yellow-Green 151C.

*Venation.*—Type: Pinnate. Venation color upper side: Near RHS Red-Purple 71A in Red-Purple center. Veins not visible in Yellow-Green margins. Venation color under side: Near RHS Greyed-Purple 186B in Greyed-Purple center. Veins not visible in Yellow-Green margins.

Petiole:

*Length.*—Average 9 mm.

*Diameter.*—Average 4 mm.

*Color.*—Near RHS Yellow-Green 151D.

*Texture.*—Glabrous.

INFLORESCENCE

Natural flowering season: Floral initiation begins in mid-August at 41N latitude, natural daylength.

Inflorescence type and habit: Terminal raceme.

Individual flowers: Zygomorphic flowers facing outward.

Longevity of individual flowers: About 3 weeks.

Fragrance: None

Inflorescence size:

*Length.*—7 to 12 cm.

*Width.*—4 cm.

Quantity of flowers per inflorescence: About 30 to 60.

Corolla:

*Shape*.—Bilabiate, tubular.

*Aspect*.—Outward

*Persistence*.—Self-cleaning.

*Size*.—About 19 mm long and 4 mm wide.

Petals:

*Upper lip*.—Width: 8 mm. Length: 6 mm. Apex: Obtuse, rounded, composed of 2 fused lobes. Base: Fused to central petal. Margin: Entire. Texture: Front: Glabrous. Back: Glabrous. Color: Upper surface: RHS Violet-Blue 91D. Lower surface: RHS Violet-Blue 91D.

*Lower lip*.—Width: 6 mm (folded). Length: 1.2 cm. Apex: Obtuse, rounded. Base: Fused. Margin: Entire. Texture: Front: Glabrous. Back: Glabrous. Color: Upper surface: RHS Violet-Blue N89C. Base 91D. Lower surface: RHS Violet-Blue 90D. Base White N155A.

*Tube*.—Diameter: 3 mm. Length: 6 mm. Color: Inner: RHS Violet-Blue 91D. Outer: RHS Violet-Blue 91D. Texture: Glabrous.

Bud:

*Shape*.—Ovate.

*Color*.—Base Violet-Blue 91D, apex 90A.

*Size*.—6 mm in height and 4 mm in diameter.

*Texture*.—Glabrous.

Calyx: Bell-shaped, composed of 5 sepals fused at base.

Sepals:

*Shape*.—Elliptic.

*Apex*.—Acute.

*Base*.—Fused.

*Margin*.—Entire.

*Length*.—5 mm.

*Width*.—3 mm.

*Texture*.—Glabrous, upper and lower surfaces.

*Color*.—Upper surface: RHS Yellow-Green 145A. Lower surface: RHS Yellow-Green 145B.

Peduncle:

*Shape*.—Quadrate with prominent longitudinal veins.

*Length*.—2 to 5 cm.

*Diameter*.—4 mm.

*Strength*.—Medium.

*Texture*.—Glabrous.

*Color*.—RHS Yellow-Green N144D.

Pedicel:

*Orientation*.—45° to 90° from peduncle.

*Texture*.—Glabrous.

*Length*.—4 to 7 mm.

*Diameter*.—2 mm.

*Color*.—RHS Yellow-Green 144B.

*Strength*.—Medium.

REPRODUCTIVE ORGANS

Androecium:

*Number of stamens*.—4 per flower, non-protruding.

*Filament*.—Unfused segment about 4 mm in length, colored near White N155C.

*Pollen*.—Not observed.

Gynoecium:

*Pistil number*.—1 per flower.

*Pistil length*.—14 mm

*Style length*.—8 mm

*Style color*.—RHS White N155C.

*Stigma shape*.—Two-parted

*Stigma color*.—White N155C.

*Ovary color*.—RHS Yellow-Green N144D.

OTHER CHARACTERISTICS

Disease and pest resistance: Neither resistance nor susceptibility to diseases or pests normal to *Coleus* have been observed in this variety.

Drought tolerance and temperature tolerance: Tender perennial, USDA zones 10-11. Summer annual in colder zones.

Fruit/seed production: Not observed to date.

What is claimed is:

1. A new and distinct cultivar of *Coleus* plant named 'G20057' as herein illustrated and described.

* * * * *